United States Patent [19]

Clark

[11] 4,402,907
[45] Sep. 6, 1983

[54] TRIAZINE CARBOXYLIC ACIDS AS CORROSION INHIBITORS FOR AQUEOUS SYSTEMS

[75] Inventor: David R. Clark, Sale, England

[73] Assignee: Ciba-Geigy Corporation, Ardsley, N.Y.

[21] Appl. No.: 289,583

[22] Filed: Aug. 3, 1981

[30] Foreign Application Priority Data

Aug. 13, 1980 [GB] United Kingdom ............... 8026311

[51] Int. Cl.³ .............................................. C23F 11/00
[52] U.S. Cl. ........................................ 422/7; 252/391; 252/392; 252/390; 252/389 R; 252/79; 106/14.15; 106/14.18; 422/16; 422/17; 210/698
[58] Field of Search ............... 252/390, 391, 392, 394, 252/73, 76, 77, 79; 148/180, 6.14 R; 210/58, 59; 422/14, 7, 16; 106/14.05, 14.11, 14.15, 14.16, 14.18; 544/196, 197

[56] References Cited

U.S. PATENT DOCUMENTS

| | | | |
|---|---|---|---|
| 2,485,309 | 10/1949 | Nunn | 252/392 |
| 3,165,515 | 1/1965 | D'Alelio | 260/248 |
| 3,236,846 | 2/1966 | Knusli et al. | 260/249.8 |
| 3,697,520 | 10/1972 | Winter | 260/249.6 |
| 3,897,209 | 7/1975 | Harris et al. | 21/2.7 R |
| 3,925,245 | 12/1975 | Harris et al. | 252/389 A |
| 3,963,636 | 6/1976 | Harris et al. | 252/181 |
| 4,089,796 | 5/1978 | Harris et al. | 252/181 |

FOREIGN PATENT DOCUMENTS 1935010 1/1971 Fed. Rep. of Germany.
2819796 11/1978 Fed. Rep. of Germany.

OTHER PUBLICATIONS

Nestler et al., J. Prakt Chem., 23, 173-185 (1963).
Lastovskii et al., Zhur. Anal. Khim, 15, 419-423 (1960).

*Primary Examiner*—Josephine Barr
*Attorney, Agent, or Firm*—Harry Falber

[57] ABSTRACT

Triazine di- and tricarboxylic acids of the formula

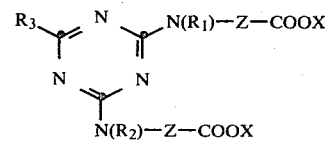

wherein Z is a straight-chain or branched chain unsubstituted or substituted 1-11C alkylene group, a 2 or 3C alkenylene group, a 5-12C cycloalkylene group or an unsubstituted or substituted arylene group, X is H, an alkali metal, an alkaline earth metal, $NH_4^+$ or a primary, secondary or tertiary 1-12C ammonium residue, $R_1$ and $R_2$ are the same or different and each is H, 1-4C alkyl or a group —Z—COOX or $R_1$ or $R_2$ together with Z can form a 5- or 6-membered heterocyclic ring, $R_3$ is 1-12C alkyl, phenyl or a group of formula —$NR_4R_5$, —$OR_6$ or —$SR_6$ in which $R_4$ and $R_5$, independently, are H, 1-12C alkyl optionally substituted by a hydroxyl group, cyclohexyl, an aryl group having from 6 to 10 ring carbon atoms, optionally substituted or a group —Z—COOX and $R_6$ is H, 1-12C alkyl, or a 6-12C aryl group, are excellent corrosion inhibitors for aqueous systems in contact with ferrous metals. Such systems may be e.g. water circuits, aqueous machining fluids or any other aqueous functional fluids.

9 Claims, No Drawings

TRIAZINE CARBOXYLIC ACIDS AS CORROSION INHIBITORS FOR AQUEOUS SYSTEMS

The present invention relates to a method of inhibiting corrosion of ferrous metals in contact with an aqueous system by adding certain triazine carboxylic acids or their water-soluble salts to the aqueous system. It further relates to a composition comprising an aqueous system in contact with a ferrous metal and, as corrosion inhibitor, a triazine carboxylic acid or a salt thereof.

In recent years, a great deal of technical effort has been directed towards coping with the problems associated with inhibiting the corrosion and/or rusting of metal in contact with water circulating systems. Various corrosion-inhibiting compositions have been proposed, e.g. those described in British Patent Specification No. 1,374,270, using mixtures of organic materials with zinc salts; and in U.S. Pat. No. 3,133,028, using mixtures of thiocyanates or thioureas with chromates. Such known compositions are associated, however, with certain disadvantages. For instance, the use of heavy metals such as chromium and zinc creates effluent problems because of their toxicity; and environmental restrictions have brought about a search for alternatives. Other synergistic corrosion-inhibiting mixtures containing no heavy metals are known e.g. those disclosed in British Patent Specification No. 1,392,044, using synergistic mixtures of amino phosponic acids and nitrites. These compositions have the disadvantage that, under operating conditions, the nitrite component can be oxidised to nitrate, thus reducing the efficiency of the inhibitor, and promoting microbiological growth or the nitrite can interact with amines to form toxic N-nitroso compounds.

We have now found that certain triazine carboxylic acids and their water-soluble salts are excellent corrosion inhibitors when used in aqueous systems such as water circulating systems. Moreover, these triazine carboxylic acids also exhibit excellent corrosion inhibition when used in other aqueous systems such as aqueous machining fluids, antifreeze fluids, water/glycol hydraulic fluids and water-based surface coating formulations.

According to the present invention, the corrosion of ferrous metals in contact with an aqueous system is inhibited by adding to the aqueous system as corrosion inhibitor, a compound having the formula:

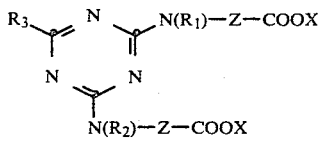

wherein Z is a straight- or branched chain alkylene group having from 1 to 11, preferably 1 to 5, carbon atoms, an alkenylene group having 2 or 3 carbon atoms, a cycloalkylene group having from 5 to 12 carbon atoms or an arylene group having from 6 to 10 ring carbon atoms, preferably phenylene or naphthylene; each of the above aliphatic- or cycloaliphatic groups Z being preferably unsubstituted but optionally substituted by one or more OH, SH or 1-4C carboxyalkyl groups and/or interrupted by one or more O or S atoms or

or $>NR'$ groups wherein $R'$ is H, 1–4C alkyl or 1–4C carboxyalkyl, and wherein the aromatic groups Z are preferably unsubstituted but are optionally substituted by one or more 1–4C alkyl groups, OH, 1–4C alkoxy, thio, 1–4C alkylthio, carboxylic or sulphonic acid groups; X is H, an alkali metal, an alkaline earth metal, $NH_4^+$ or a primary-, secondary- or tertiary ammonium residue containing from 1 to 12 carbon atoms and optionally substituted with one or more hydroxyl groups; $R_1$ and $R_2$ are the same or different and each is H, 1–4C alkyl or a group $-Z-COOX$ wherein Z and X have their previous significance; or when Z is alkylene or alkenylene, $R_1$ or $R_2$ together with Z and the nitrogen atom to which they are attached can form a 5- or 6-membered heterocyclic ring e.g. a pyrrolidine, piperidine or piperazine ring, preferably $R_1$ and $R_2$ are H or $CH_3$; $R_3$ is 1–12 C alkyl, phenyl or a group of formula $-NR_4R_5$, $-OR_6$ or $-SR_6$ in which $R_4$ and $R_5$, independently, are H, 1–12C alkyl optionally substituted by a hydroxyl group, a cyclohexyl group, an aryl group having from 6 to 10 ring carbon atoms, preferably phenyl or naphthyl, optionally substituted by one or more 1–4C alkyl groups, OH, 1–4C alkoxy, thio, 1–4C alkylthio, carboxylic or sulphonic acid groups, a group $-Z-COOX$ wherein Z and X have their previous significance, or $R_4$ and $R_5$ and the N atom to which they are attached can form a 5–7 membered heterocyclic ring optionally interrupted by other heteroatoms e.g. a pyrrolidine, piperidine, morpholine or piperazine ring, and $R_6$ is H, 1–12C alkyl, or an aryl group having from 6 to 10 ring carbon atoms, preferably phenyl.

Preferably, $R_3$ is a group $-NR_4R_5$ wherein $R_4$ is $-Z-COOX$ or alkyl and $R_5$ is H or alkyl.

Preferably, Z is unsubstituted 1–11C alkylene. Examples of alkylene groups Z include methylene, ethylene-1,2-, propylene-1,2, propylene-1,3-, butylene-1,4-, pentylene-1,5-, hexylene-1,6-, 1,1-dimethylethylene-1,2, octylene-1,8-, decylene-1,10-, and undecylene-1,11- groups. Especially preferably is Z an unsubstituted 1–5C alkylene group.

When X is an alkali metal, it may be sodium, potassium or lithium; examples of alkaline earth metals X include calcium or magnesium; and 1–12C optionally hydroxyl-substituted protonated amine residues X include methylamine-, ethylamine-, isopropylamine-, dibutylamine-, tributylamine-, octylamine-, dodecylamine-, and mono-, di- and triethanolamine residues. Preferably X is hydrogen, an alkali metal or mono-, di- or triethanolammonium.

Alkyl groups $R_4$, $R_5$ and $R_6$ are e.g. methyl, ethyl, propyl, butyl, hexyl, octyl, decyl or dodecyl groups.

Specific compounds of formula I which may be used in the compositions of the invention include:
2,4,6-tris(5'-carboxypentylamino)-1,3,5-triazine
2,4,6-tris(carboxymethylamino)-1,3,5-triazine
2,4,6-tris(3'-carboxypropylamino)-1,3,5-triazine
2,4,6-tris(2'-carboxyethylamino)-1,3,5-triazine
2,4,6-tris(4'-carboxybutylamino)-1,3,5-triazine
2,4,6-tris(11'-carboxyundecylamino)-1,3,5-triazine
2,4,6-tris(5'-carboxypentyl-N-methylamino)-1,3,5-triazine
2,4,6-tris(carboxymethyl-N-methylamino)-1,3,5-triazine 2,4,6-tris(3'-carboxypropyl-N-methylamino)-1,3,5-triazine
2,4,-bis(5'-carboxypentylamino)-6-ethylamino-1,3,5-triazine
2,4,-bis(5'-carboxypentylamino)-6-n-octylamino-1,3,5-triazine
2,4-bis(5'-carboxypentylamino)-6-cyclohexylamino-1,3,5-triazine
2,4-bis(5'-carboxypentylamino)-6-diethylamino-1,3,5-triazine
2,4-bis(5'-carboxypentylamino)-6-(2''-hydroxyethylamino)-1,3,5-triazine
2,4-bis(2'-carboxyethylamino)-6-n-octylamino-1,3,5-triazine
2,4-bis(2'-carboxyethylamino)-6-diethylamino-1,3,5-triazine
2,4-bis(2'-carboxyethylamino)-6-butylamino-1,3,5-triazine
2,4-bis(2'-carboxyethylamino)-6-ethylamino-1,3,5-triazine
2,4-bis(5'-carboxypentylamino)-6-anilino-1,3,5-triazine
2,4-bis(3'-carboxypropylamino)-6-ethylamino-1,3,5-triazine
2,4-bis(3'-carboxypropylamino)-6-n-octylamino-1,3,5-triazine
2,4-bis(3'-carboxypropylamino)-6-n-propylamino-1,3,5-triazine
2,4-bis(carboxymethyl)-6-n-octylamino-1,3,5-triazine
2,4-bis(carboxymethyl)-6-cyclohexylamino-1,3,5-triazine
2,4-bis(carboxymethyl)-6-dodecylamino-1,3,5-triazine
2,4-bis(5'-carboxypentyl-n-methylamino)-6-ethylamino-1,3,5-triazine
2,4-bis(3'-carboxypropyl-N-methylamino)-6-n-octylamino-1,3,5-traizine
2,4-bis(carboxymethyl-N-methylamino)-6-n-octylamino-1,3,5-triazine
2,4-bis(2'-carboxyethyl-N-methylamino)-6-n-octylamino-1,3,5-triazine
2,4-bis(5'-carboxypentylamino)-6-(2''-carboxyethylamino)-1,3,5-triazine
2,4-bis(5'carboxypentylamino)-6-(carboxymethylamino)-1,3,5-triazine
2,4-bis(3'-carboxypropylamino)-6-(2''-carboxyethylamino)-1,3,5-triazine
2,4-bis(2'-carboxyethylamino)-6-(5''-carboxypentylamino)-1,3,5-triazine
2,4-bis(3'-carboxypropylamino)-6-(5''-carboxypentylamino)-1,3,5-triazine
2,4-bis(5'-carboxypentylamino)-6-methoxy-1,3,5-triazine
2,4-bis(2'-carboxyethylamino)-6-butylthio-1,3,5-triazine
2,4-bis(5'-carboxypentylamino)-6-n-octyloxy-1,3,5-triazine
2,4-bis(3'-carboxypropylamino)-6-n-dodecylthio-1,3,5-triazine
2,4-bis(2'-carboxyethylamino)-6-phenoxy-1,3,5-triazine
2,4-bis(5'-carboxypentylamino)-6-methylthio-1,3,5-triazine
2,4-bis(5'-carboxypentylamino)-6-ethoxy-1,3,5-triazine
as well as the water-soluble salts thereof.

The compounds of formula I are not new, their production having been described e.g. in a paper by Dyatlova et al., Zhurnal Analiticheskoi Khimii, Vol. 15, No. pp 419-423, July-August 1960; in Offenlegungsschrift 1935010; in Offenlegungsschrift 2819796; in U.S. Pat. No. 3,697,520; and in a paper by Nestler et al. in J. Prakt. Chem. Vol. 23, Part 3-4, pp. 173-85, 1963. However, none of these disclosures describes or suggests the use of the compounds of formula I as a corrosion inhibitor for ferrous metals in aqueous systems.

Preferably, the composition of the present invention contains from 0.001% to 5% by weight of a compound of formula I, based on the total weight of the composition.

As mentioned hereinbefore, examples of aqueous systems which may form a component of the compositions of the present invention include water circulating systems; aqueous machining fluid formulations (e.g. for use in boring, milling, reaming, turning, cutting, sawing, grinding, and thread-cutting operations or in non-cutting shaping in drawing or rolling operations); aqueous glycol antifreeze systems; water/glycol hydraulid fluids; and aqueous-based surface coating systems e.g. emulsion paints or aqueous powder coatings.

In the aqueous systems of the invention the compounds of formula I may be used singly or in admixture with other additives. Examples of such co-additives in water circulating systems are known corrosion inhibitors such as phosphonates, phosphonocarboxylic acids, phosphinocarboxylic acids, as well as N-acyl sarcosines, imidazolidines, triethanolamine and fatty amines and polycarboxylic acids; water-soluble azoles e.g. triazoles such as benzotriazole, methylene bis-benzotriazole and other copper-passivating derivatives, e.g. 2-mercaptobenzothiazole. Further preferred co-additives are dispersing and/or threshold agents, such as for example polymerised acrylic acid and its salts, hydrolysed polyacrylonitrile, polymerised methacrylic acid and its salts, polyacrylamide and copolymers thereof from acrylic and methacrylic acids, lignin sulphonic acid and its salts, tannin, naphthalene sulphonic acid/formaldehyde condensation products, starch and its derivatives, and cellulose. Specific threshold agents such as, for example, alkyl phosphonic acids, 1-aminoalkyl-1,1-diphosphonic acids and their salts, polycarboxylic acids e.g. polymaleic acids and alkali metal phosphates, may also be used together with the compounds of formula I.

Precipitating agents such as alkali metal orthophosphates, carbonates; oxygen scavengers such as alkali metal sulphites and hydrazines; sequestering agents such as nitrilotriacetic acid and their salts, ethylene diamine tetraacetic acid and its salts; antifoaming agents such as distearylsebacamide, distearyl adipamide and related products derived from ethylene oxide and/or propylene oxide condensations, in addition to fatty alcohols, such as capryl alcohols and their ethylene oxide condensates; may also be used together with the compounds of formula I.

In the aqueous compositions of the invention in which the aqueous system component is an aqueous machining fluid formulation, such formulation may be a water dilutable cutting or grinding fluid such as:
(a) Aqueous concentrates of one or more corrosion inhibitors, and optionally one or more anti-wear additives, used at dilutions of 1:50 to 1:100, which are usually employed as grinding fluids;
(b) Polyglycols containing biocides, corrosion inhibitors and anti-wear additives which are used at dilutions of 1:20 to 1:40 for cutting operations and 1:60 to 1:80 for grinding;
(c) Semi-synthetic cutting fluids similar to (b) but containing in addition 10 to 25% oil with sufficient emulsifier to render the water diluted product translucent;
(d) An emulsifiable mineral oil concentrate containing, for example, emulsifiers, corrosion inhibitors, extreme pressure/antiwear additives, biocides, antifoaming agents, coupling agents etc; they are generally diluted from 1:10 to 1:50 with water to a white opaque emulsion;

(e) A product similar to (d) containing less oil and more emulsifier which on dilution to the range 1:50 to 1:100 gives a translucent emulsion for cutting or grinding operations.

Mixtures of sodium nitrite and triethanolamine have been used to inhibit corrosion in metal working but because of related toxicity problems and because of legal regulations in some countries relating to effluents, industry is moving away from the use of sodium nitrite.

For those aqueous systems of the invention in which the aqueous system component is an aqueous machining fluid formulation, an anti-freeze or a water/glycol hydraulic fluid, the compounds of formula I may be used singly, or in admixture with other additives e.g. known corrosion inhibitors and, for the machining fluids, an extreme-pressure additive.

Examples of other corrosion inhibitors which may be present in the aqueous systems of the present invention in addition to the amine salts of the compounds of formula I include the following groups:

(a) Organic acids, their esters or ammonium, amine, alkanolamine and metal salts, for example, benzoic acid, p-tert.butyl benzoic acid, disodium sebacate, triethanolamine laurate, iso-nonanoic acid, triethanolamine salt of (p-toluene sulphonamido caproic acid), sodium N lauroyl sarcosinate or nonyl phenoxy acetic acid;

(b) Nitrogen containing materials such as the following types: fatty acid alkanolamides; imidazolines, for example 1-hydroxy-ethyl-2-oleylimidazoline; oxazolines; triazoles for example benzotriazoles; and inorganic salts, for example sodium nitrite and nitrate;

(c) Phosphorus containing materials such as the following types: amine phosphates, phosphonic acids or inorganic salts, for example sodium dihydrogen phosphate;

(d) Sulphur containing compounds such as the following types: sodium, calcium or barium petroleum sulphonates, or heterocyclics for example sodium mercaptobenzothiazole.

Examples of extreme pressure additives which may be present in the fluids of the present invention include sulphur and/or phosphorus and/or halogen containing materials, for instance sulphurised sperm oil, sulphurised fats, tritolyl phosphate, chlorinated paraffins or ethoxylated phosphate esters.

The following Examples further illustrate the present invention. Parts and percentages are by weight unless otherwise stated.

The following Examples 1 to 15 illustrate the production of certain compounds of formula I which are useful as a corrosion inhibitor in the compositions of the invention.

Example 1

2,4,6-Tris(5'-carboxypentylamino)-1,3,5-triazine (Method A)

To a slurry of 18.5 parts of cyanuric chloride in 150 parts of water at 0.5° C. is added one third of a solution of 49 parts of 6-aminohexanoic acid sodium salt in 70 parts of water over 1½ hours, maintaining the temperature at <5° C. The remainder of the solution of the amino acid is then added and the reaction mixture allowed to warm to room temperature. After stirring at room temperature for 2 hours, the mixture is heated slowly to boiling and refluxed for 3 hours. During this period, the pH of the mixture is maintained between 10 and 11 by the addition of 25% w/w sodium hydroxide solution. After cooling to 50° C., the cloudy solution is filtered the volume increased to approximately 1300 ml by the addition of 1 liter water and then acidified to pH 4–4.5 with concentrated hydrochloric acid whereupon a white crystalline solid precipitates. The mixture is allowed to cool to room temperature and filtered. After washing thoroughly with cold water, the product is dried in a vacuum oven yielding 35 parts of 2,4,6-tris(5'-carboxypentylamino)-1,3,5-triazine (75%). This may be recrystallised from acetic acid-water giving a product having m.pt 177° C.

$C_{21}H_{36}N_6O_6$ requires: C 53.85%; H 7.69%; N 1795%; found: C 54.07%; H 7.68%; N 17.26%

Examples 2–7, shown in Table I, were prepared by the same procedure A.

Example 8

2-n-Octylamino-4,6-bis(2'-carboxyethylamino)-1,3,5-triazine (Method B)

18.5 parts of cyanuric chloride are treated with 200 parts of acetone and the opaque solution added to 300 parts ice-water. To the suspension of freshly precipitated cyanuric chloride at 0°–5° C. are added 28 parts n-octylamine over 1 hour maintaining the pH at 5–6 by concomitant addition of 25% w/w sodium hydroxide solution. A solution of 42.4 parts of β-alanine sodium salt in 60 parts water and the reaction mixture allowed to rise to room temperature at which it was stirred for 2 hours. The mixture is heated slowly to 95° C. during which time acetone is removed by distillation and the pH maintained at 10–11 by addition of 25% sodium hydroxide solution. The reaction is completed by heating at 95°–100° C. for six hours at pH 10–11. The solution is cooled to 30° C. and acidified to pH 4–4.5 with concentrated hydrochloric acid to precipitate a white crystalline solid which is filtered, washed with water, and dried in a vacuum oven yielding 26.4 parts 2-n-octylamino-bis(2'-carboxyethylamino)-1,3,5-triazine (69%). This may be recrystallised from water-acetic acid giving a product m.pt 138°–140° C.

$C_{11}H_{30}N_6O_4$ requires: C 53.40%; H 7.85%; N 21.99%; found: C 52.91%; H 7.97%; N 21.65%

Examples 9–15, shown in Table I, were prepared by the same procedure B.

TABLE I

Production of Tris aminotriazines of formula:

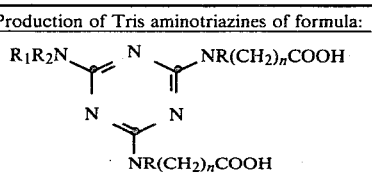

| Example | R | $R_1$ | $R_2$ | n | Yield (%) | M. pt. (°C.) | | Elemental analysis (%) | C | H | N |
|---|---|---|---|---|---|---|---|---|---|---|---|
| 2 | H | $(CH_2)_3COOH$ | H | 3 | 67 | 205.7 | $C_{15}H_{24}N_6O_6 \cdot H_2O$ | R | 44.77 | 6.47 | 20.90 |
|   |   |   |   |   |   |   |   | F | 44.60 | 6.33 | 20.48 |
| 3 | H | $(CH_2)_2COOH$ | H | 2 | 73 | >230 | $C_{12}H_{18}N_6O_6$ | R | 42.11 | 5.26 | 24.56 |
|   |   |   |   |   |   |   |   | F | 42.24 | 5.27 | 24.24 |
| 4 | H | $CH_2COOH$ | H | 1 | 92 | >230 | $C_9H_{12}N_6O_6$ | R | 36.00 | 4.00 | 28.00 |
|   |   |   |   |   |   |   |   | F | 35.13 | 3.95 | 27.44 |
| 5 | $CH_3$ | $(CH_2)_5COOH$ | $CH_3$ | 5 | 45 | 109–11 | $C_{24}H_{42}N_6O_6$ | R | 56.47 | 8.24 | 16.47 |
|   |   |   |   |   |   |   |   | F | 56.23 | 7.84 | 16.97 |
| 6 | $CH_3$ | $(CH_2)_3COOH$ | $CH_3$ | 3 | 61 | 146–7 | $C_{18}H_{30}N_6O_6$ | R | 50.70 | 7.04 | 19.72 |
|   |   |   |   |   |   |   |   | F | 51.15 | 7.10 | 19.68 |
| 7 | $CH_3$ | $CH_2COOH$ | $CH_3$ | 1 | 65 | 225–6 | $C_{12}H_{18}N_6O_6$ | R | 42.11 | 5.26 | 24.56 |
|   |   |   |   |   |   |   |   | F | 41.80 | 5.11 | 24.10 |
| 9 | H | $n\text{-}C_8H_{17}$ | H | 3 | 78 | 174–6 | $C_{19}H_{34}N_6O_4$ | R | 55.59 | 8.35 | 20.48 |
|   |   |   |   |   |   |   |   | F | 55.46 | 8.51 | 20.54 |
| 10 | H | $n\text{-}C_8H_{17}$ | H | 5 | 69 | 119–21 | $C_{23}H_{42}N_6O_4$ | R | 59.23 | 9.01 | 18.03 |
|   |   |   |   |   |   |   |   | F | 59.06 | 8.97 | 18.05 |
| 11 | H | $C_2H_5$ | H | 2 | 73 | 229–31 | $C_{11}H_{18}N_6O_4$ | R | 44.30 | 6.04 | 28.18 |
|   |   |   |   |   |   |   |   | F | 43.63 | 6.01 | 27.66 |
| 12 | H | $C_2H_5$ | $CH_3$ | 2 | 73 | 208.10 | $C_{13}H_{22}N_6O_4$ | R | 47.85 | 6.75 | 25.77 |
|   |   |   |   |   |   |   |   | F | 46.85 | 6.84 | 24.25 |
| 13 | H | $C_2H_5$ | H | 3 | 63 | 192–4 | $C_{13}H_{22}N_6O_4$ | R | 47.85 | 6.75 | 25.77 |
|   |   |   |   |   |   |   |   | F | 46.72 | 7.09 | 25.39 |
| 14 | H | $C_2H_5$ | H | 5 | 79 | 150–2 | $C_{17}H_{30}N_6O_4$ | R | 53.40 | 7.85 | 21.99 |
|   |   |   |   |   |   |   |   | F | 52.19 | 8.08 | 21.00 |
| 15 | H | $C_2H_5$ | $C_2H_5$ | 5 | 66 | 149–51 | $C_{19}H_{34}N_6O_4$ | R | 55.61 | 8.29 | 20.49 |
|   |   |   |   |   |   |   |   | F | 54.61 | 7.70 | 19.84 |

R = requires
F = found

Examples 16 to 30

The corrosion inhibitor activity of the compounds synthesized in Examples 1 to 15 was demonstrated in the Aerated Solution Bottle Test using, as test water:

(A) a synthetic corrosive water (pH 7.5, hardness 30 ppm $CaCO_3$)
(B) an acid-dosed water (pH 6.5, hardness 200 ppm $CaCO_3$)
(C) a base-exchanged water (pH 7.5, hardness zero).

Mile steel coupons, measuring 5 cm×2.5 cm×0.1 cm scrubbed with pumice, immersed for one minute in hydrochloric acid and then rinsed, dried and weighed.

The desired proportion of the corrosion inhibitor (100 ppm) under test was then dissolved in the test water.

A mile steel coupon is suspended in the solution, and the whole is stored in a bottle in a thermostat at 40° C. During the storage period, air is passed into the solution at 500 ml/minute, the passage of the air being screened from the mild steel coupon; any water losses by evaporation are replaced as they occur with distilled water from a constant head apparatus.

After 48 hours, the mild steel coupon is removed, scrubbed with pumice, immersed for one minute in hydrochloric acid inhibited with 1% by weight of hexamethylenetetraamine and then rinsed, dried and reweighed. A certain loss in weight was observed to have occurred. A blank test i.e. immersion of a mild steel specimen in the test water in the absence of any potential corrosion inhibitor, is carried out with each series of tests. The corrosion rates are calculated in milligrams of weight loss/sq. decimeter/day (m.d.d.) but for convenience the results are shown as percentages protection, which is defined as follows:

$$\% \text{ Protection} = \frac{\text{Blank corrosion rate (in } mdd\text{)} - \text{Sample corrosion rate (in } mdd\text{)}}{\text{Corrosion rate for blank (in } mdd\text{)}} \times 100$$

The results obtained are set out in the following Table II

TABLE II

| Example | Sodium salt of compound of Example | % Protection in test water A | B | C |
|---|---|---|---|---|
| 16 | 1 | 95 | 95 | 93 |
| 17 | 2 | 100 | 96 | 98 |
| 18 | 3 | 99 | 96 | 97 |
| 19 | 4 | (40) | (23) | 92 |
| 20 | 5 | 55 | 86 | 96 |
| 21 | 6 | 86 | (28) | 97 |
| 22 | 7 | 76 | (30) | 74 |
| 23 | 8 | 63 | 89 | 100 |
| 24 | 9 | 60 | (15) | 98 |
| 25 | 10 | 96 | 100 | 100 |
| 26 | 11 | 90 | 86 | 96 |
| 27 | 12 | — | — | 100 |
| 28 | 13 | 86 | 96 | 97 |
| 29 | 14 | 70 | 100 | 100 |
| 30 | 15 | 97 | 95 | 100 |

The results demonstrate the excellent corrosion inhibition exhibited by the compositions of the present invention.

Examples 31 to 33

Evaluation of corrosion inhibition by a laboratory heat exchanger rig test

In this rig, corrosive water is aerated and circulated over a number of metal coupons, and is heated by being passed through a heated steel heat exchanger tube. After a suitable test period, the metal coupons and the heat exchanger tube are examined, and their state assessed.

In detail, the rig consists of a closed water circuit, made up of the following items in order,
20 liter reservoir
1 liter reservoir
flow meter
coupon chamber
heat exchanger
cooling condenser.

Corrosive water in the 20 liter reservoir is aerated with compressed air introduced through a sintered disc at about 5 liters per minute, and is then pumped to the 1 liter reservoir. From this reservoir it is pumped through the flow meter to the glass coupon chamber in which are a numer of rectangular metal coupons each 2.5 by 5.0 cms. mounted on a perspex jig. The water then flows through the heat exchanger which is made up of a 1.58 cm internal diameter steel tube with copper and pieces around which is wound a 960 watt heater coil; from the heat exchanger the water flows through the cooling condenser back to the 20 liter reservoir.

A flow rate in the circuit of about 4.55 liters per minute provides a velocity of about 0.46 meter per second and a Reynolds number of 8500 in the heat exchanger. The heater coil gives the heat exchanger tube a skin temperature of about 60° C. and the water leaves at about 45° C., a difference across the heat transfer surface of some 15° C. The cooling condenser is so operated as to cool the water to about 40° C. before it begins a fresh circuit.

Metal coupons are scrubbed with pumice and then immersed in acid as follows:

| Metal | Acid |
|---|---|
| mild steel | Conc. HCl diluted 1:1 with water at room temperature for 1 minute |
| copper | Conc. HCl diluted 1:1 with water at room temperature for 1 minute |
| brass | Conc. HCl diluted 1:1 with water at room temperature for 1 minute |
| aluminium | 5% phosphoric acid/2% Chromic acid, at 75° C. |
| | for 5 minutes. |

After such immersion, the coupons are rinsed with water, dried and weighed; they are then mounted on a perspex jig, care being taken to ensure that none of the coupons touch each other, and that they are insulated from the bolt holding the jig together. The heat exchanger tube is cleand with pumice, dipped in conc. hydrochloric acid diluted 1:1 with water, and then rinsed in water and dried.

The rig is assembled, and cleaned thoroughly by circulating conc. hydrochloric acid diluted 1:1 with water, then flushing with tap water for about half-an-hour (about 136.4 liters in all) and draining. The necessary quantity of additives to produce the desired concentrations is put into one of the reservoirs and the rig is filled with 22 liters of a standardized Manchester corrosive test water.

The pump is primed and started, and the heater switched on.

The concentration of inhibitor and the water level in the rig are checked daily.

After three days, and again after ten days, the heat exchanger tube is removed, sectioned and examined. The test coupons are removed and the mild steel, brass and copper coupons are cleaned as before except that the acid is inhibited with 1% hexamine, rinsed, dried and reweighed. The aluminium specimens are scrubbed, dried and reweighed.

The results observed enable an assessment to be made of the anti-corrosive action of the inhibitor under test, using the same parameter of corrosion rate (in mdd) as was used in Examples 16 to 30 and demonstrate the high effectivity of the compounds of the invention as corrosion inhibitors in a water circulating rig.

TABLE III

Cooling water corrosion inhibition;
Mk Rig Results
[Treatment dosage: 100 ppm/3 days followed by 25 ppm/10 days]

| Example | Sodium salt of compound of Example | Water conditions | Corrosion rate (mdd) | | | | |
|---|---|---|---|---|---|---|---|
| | | | Mild steel | Al | Cu | Brass | MSHE |
| 31 | BLANK | Manchester water, pH 7.0, 40° C. | 140.1 | 5.8 | 3.7 | 4.8 | 420.6 |
| | 1 | " | 2.5 | 2.7 | 0.9 | 2.0 | 39.8 |
| 32 | BLANK | Base-exchange water, pH 8.0, 40° C. | 139.9 | 0.0 | 1.0 | 1.8 | 485.3 |
| | 1 | " | 6.4 | 4.0 | 0.9 | 0.5 | 11.2 |
| 33 | BLANK | Macclesfield water, pH 6.5, 40° C. | 67.8 | 8.2 | 0.6 | 0.5 | 215.4 |
| | 1 | " | 19.9 | 0.0 | 1.1 | 0.9 | 38.5 |

MSHE is a mild steel heat exchanger

Examples 34 to 38

The corrosion resistance of various aqueous cutting fluid compositions of the invention were assessed by the following procedure, which is a modification of the Institute of Petroleum Test 287.

A 1% solution of the compound under test is prepared and contains sufficient triethanolamine (TEA) that the solution has a pH value of 9.

This solution is further diluted by a factor of 2, 4, 8 or 16 and each of the solutions so obtained is contactes with cast iron chips-placed on a filter paper according to the method set forth in the IP 287 Test Procedure.

The visual assessment of the condition of the filter paper after 2 hours exposure is in accordance with the following guidelines:

| degree of rusting | rating |
|---|---|
| no rusting | 0 |
| ≦5 small specks | T (trace) |
| ≦10% area rusted | M (moderate) |
| >10% area rusted | S (severe) |

TABLE IV

| Example | Compound of Example | % TEA for 1% of the Compound of Example | pH | Dilution Ratio | IP 287 Test Rust (deionised/H$_2$O) | Rust (hard/H$_2$O) | Sensitivity to hard water |
|---|---|---|---|---|---|---|---|
| 34 | 1 | 4.4 | 8.8 | 1:38 | 0 | 0 | 0 |
|   |   |   |   | 1:76 | 0 | 0 |   |
|   |   |   |   | 1:152 | 0 | T-M |   |
|   |   |   |   | 1:304 | T-M | — |   |
| 35 | 5 | 5.7 | 9.1 | 1:30 | 0 | 0 | 0 |
|   |   |   |   | 1:60 | 0 | 0 |   |
|   |   |   |   | 1:120 | 0 | 0 |   |
|   |   |   |   | 1:240 | T | — |   |
| 36 | 11 | 5.6 | 9.0 | 1:30 | 0 | 0 | 0 |
|   |   |   |   | 1:60 | 0 | S |   |
|   |   |   |   | 1:120 | 0 | — |   |
|   |   |   |   | 1:240 | S | — |   |
| 37 | 14 | 4.6 | 9.0 | 1:36 | 0 | 0 | 0 |
|   |   |   |   | 1:72 | 0 | 0-T |   |
|   |   |   |   | 1:144 | 0 | S |   |
|   |   |   |   | 1:288 | 0 | — |   |
| 38 | 15 | 5.5 | 9.2 | 1:31 | 0 | 0 | 0 |
|   |   |   |   | 1:62 | 0 | 0 |   |
|   |   |   |   | 1:125 | T | M |   |
|   |   |   |   | 1:248 | T | — |   |

I claim:

1. A method of inhibiting the corrosion of a ferrous metal in contact with an aqueous system which comprises incorporating in the aqueous system an effective corrosion inhibiting amount of a compound having the formula:

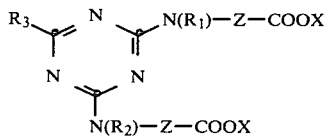

wherein Z is a straight- or branched chain 1-11C alkylene group, a 2-3C alkenylene group, a 5-12C cycloalkylene group or an arylene group, having 6-10 ring carbon atoms, the said aliphatic or cycloaliphatic groups Z being optionally substituted by one or more OH, SH or 1-4C carboxyalkyl groups and/or interrupted by one or more O or S atoms or

or >N—R' groups, wherein R' is H, 1-4C alkyl or 1-4C carboxyalkyl, and said aromatic groups Z being optionally substituted by one or more 1-4C alkyl groups, OH, 1-4C alkoxy groups, SH, 1-4C alkylthio, carboxylic or sulphonic acid groups; X is H, an alkali metal, an alkaline earth metal, NH$_4^+$, or a 1-12C primary-, secondary- or tertiary ammonium residue optionally substituted with one or more OH groups; R$_1$ and R$_2$ are the same or different and each is H, 1-4C alkyl or a group —Z—COOX wherein Z and X have their previous significance or when Z is alkylene, or alkenylene, R$_1$ or R$_2$, with Z and the nitrogen atom to which they are attached, can form a 5- or 6-membered heterocyclic ring; R$_3$ is 1-12C alkyl, phenyl or a group of formula —NR$_4$R$_5$, —OR$_6$, or —SR$_6$ in which R$_4$ and R$_5$, independently, are H, 1-12C alkyl optionally substituted by an OH group, a cyclohexyl group, an aryl group having from 6 to 10 carbon atoms, optionally substituted by one or more 1-4C alkyl groups, OH, 1-4C alkoxy, thio, 1-4C alkylthio, carboxylic or sulphonic acid groups, a group —Z—COOX wherein Z and X have their previous significance or R$_4$, R$_5$ and the N atom to which they are attached can form a 5-7 membered heterocyclic ring optionally interrupted by other hetero atoms and R$_6$ is H, 1-12C alkyl group or an aryl group having from 6 to 10 ring carbon atoms.

2. A method according to claim 1, wherein Z is a 1-11C alkylene group, X is H, an alkali metal or mono-, di- or triethanolammonium, R$_1$ and R$_2$ are H or CH$_3$ and R$_3$ is a group —NR$_4$R$_5$ wherein R$_4$ is —Z—COOX or 1-12C alkyl and R$_5$ is hydrogen or 1-12C alkyl.

3. A method according to claim 2, wherein Z is a 1-5C alkylene group, R$_3$ is a group —NR$_4$R$_5$ wherein R$_4$ is —Z—COOX or 1-8C alkyl and R$_5$ is H, CH$_3$ or C$_2$H$_5$ and X, R$_1$ and R$_2$ have the meaning given in claim 2.

4. The method according to claim 1 wherein the aqueous system is a water-circulating system; an aqueous machining fluid formulation; an aqueous glycol antifreeze system; a water/glycol hydraulic fluid; or an aqueous-based surface coating system.

5. The method according to claim 1, wherein the compound of formula I is present in admixture with a further additive.

6. The method according to claim 5 wherein the further additive is a corrosion inhibitor.

7. The method of claim 3, wherein R$_1$, R$_2$ and R$_5$ are each hydrogen.

8. The method of claim 7, wherein said compound is 2,4,6-tris(5-carboxypentylamino)-1,3,5-triazine.

9. The method of claim 1, wherein said compound is present in a concentration of from 0.001% to 5%, by weight.

* * * * *